United States Patent [19]
Cunningham

[11] Patent Number: 4,711,238
[45] Date of Patent: Dec. 8, 1987

[54] MENISCAL CUTTING DEVICE

[76] Inventor: Frank W. Cunningham, 1801 Via Estudillo, Palos Verdes Estates, Calif. 90274

[21] Appl. No.: 712,378

[22] Filed: Mar. 14, 1985

[51] Int. Cl.$^4$ .............................................. A61B 17/36
[52] U.S. Cl. ............................ 128/303.14; 128/303.17
[58] Field of Search ................... 128/6, 303.1, 303.13, 128/303.14, 303.17, 303.15, 303.16, 783, 784

[56] References Cited

U.S. PATENT DOCUMENTS

| | | | |
|---|---|---|---|
| 1,741,740 | 12/1929 | Sedehelm et al. | 128/303.15 |
| 2,022,065 | 11/1935 | Wappler | 128/6 |
| 2,056,377 | 10/1936 | Wappler | 128/303.14 |
| 2,310,844 | 2/1943 | Draeger | 128/303.14 |
| 2,447,169 | 8/1948 | Desousa | 128/303.14 |
| 2,487,502 | 11/1949 | Willinsky | 128/303.14 |
| 3,234,356 | 2/1966 | Babb | 219/233 |
| 3,494,364 | 2/1970 | Peters | 128/303.17 |
| 3,901,242 | 8/1975 | Storz . | |
| 3,903,892 | 9/1975 | Komiya | 128/303.15 |
| 3,920,021 | 11/1975 | Hiltebrandt . | |
| 3,938,527 | 2/1976 | Rioux et al. . | |
| 4,051,855 | 10/1977 | Schneiderman | 128/303.14 |
| 4,085,756 | 4/1978 | Weaver . | |
| 4,174,715 | 11/1979 | Hasson | 128/303.14 |
| 4,181,131 | 1/1980 | Ogia | 128/303.15 |
| 4,273,137 | 1/1981 | Prauoverou et al. | 128/784 |
| 4,301,802 | 11/1981 | Poler . | |
| 4,325,374 | 4/1982 | Komiya | 128/303.15 |
| 4,418,692 | 12/1983 | Guay | 128/303.14 |
| 4,474,174 | 10/1984 | Petruzzi | 128/303.15 |
| 4,485,812 | 12/1984 | Harada et al. | 128/303.15 |

FOREIGN PATENT DOCUMENTS

| | | | |
|---|---|---|---|
| 2429462 | 1/1975 | Fed. Rep. of Germany | 128/303.15 |
| 2415263 | 10/1975 | Fed. Rep. of Germany | 128/303.17 |
| 2426781 | 12/1975 | Fed. Rep. of Germany | 128/303.15 |
| 2938259 | 4/1981 | Fed. Rep. of Germany | 128/303.15 |
| 82/00084 | 1/1982 | PCT Int'l Appl. . | |

Primary Examiner—William E. Kamm
Assistant Examiner—Max F. Hindenburg
Attorney, Agent, or Firm—Gordon L. Peterson

[57] ABSTRACT

An electrosurgical meniscal cutting device including an elongated probe adapted for insertion into an incision and first and second electrode supports carried by the probe. The electrode supports are movable relative to each other to vary the spacing between them. A variable length electrode extends between the electrode supports so that the length of the electrode can be varied by varying the spacing between the electrode supports. The spacing between the electrode support is controlled to control the length of the electrode.

19 Claims, 9 Drawing Figures

MENISCAL CUTTING DEVICE

BACKGROUND OF THE INVENTION

The human knee includes a lateral meniscus and a medial meniscus between the femur and the tibia. The menisci provide stability to the knee joint. Either of the menisci may tear or split when subjected to certain forces. This injury, which is commonly referred to as torn cartilage in the knee, is painful and may limit mobility.

Torn cartilage is often treated by surgically removing the torn region of the meniscus. The surgery may be carried out, for example, with mechanical devices such as knives, scissors or rotary trimmers. However, these devices are too large to be readily usable in the very small space within the knee and are generally too slow. Also, it is difficult to reach certain regions of the meniscus with some of these devices, and the cut may be jagged.

Electrosurgery can also be used to remove the torn region of the meniscus. Electrosurgery involves the use of high-frequency current to cut tissue and/or to coagulate a vessel. Electrosurgery has been used for a variety of surgical procedures. However, one problem with using electrosurgery, or any other surgical device, for removing a region of the meniscus is that the space adjacent the menisci for carrying out the surgery is very confined. In addition, electrosurgery presents a danger of charring regions of the knee adjacent the meniscus.

One prior art electrosurgical meniscal cutting device utilizes a fixed electrode, which terminates in a free end. The exposed length of the electrode can be manually varied by moving a cannula along the electrode. However, cannula movement cannot be remotely controlled, and so the exposed length of the electrode cannot be varied remotely during surgery as would be desirable to accommodate changes in the height dimension of the meniscus. Consequently, repeated cuts may be necessary if the exposed length of the electrode is too short. Moreover, the overall length of the electrode is not variable, and so a maximum dimension of the electrode is continuously present in the confined space within the knee even when only a small portion of that length is required for cutting the thinner portions of the meniscus. Also, the electrode is not shielded during insertion so there is a danger of inadvertent burning or charring.

SUMMARY OF THE INVENTION

This invention overcomes these disadvantages by providing an electrosurgical device which includes a portion which can be made sufficiently small to work within the confined space in the knee. With this invention, charring is essentially eliminated, and cutting can rapidly take place in any direction. The resulting cut can be made with a single pass, is smooth and essentially free of jagged or irregular edges.

This invention carries out the electrosurgery with a variable length electrode. Consequently, the electrode may be made very short to facilitate insertion into the incision in the knee and thereafter extended for cutting the meniscus. Preferably, the variable electrode has a minimum length of substantially zero. Electrode length can be remotely varied as desired during surgery to accommodate various factors, such as the varying height dimension of the meniscus.

An electrosurgical cutting device constructed in accordance with this invention preferably has an elongated probe having a distal end portion adapted for insertion into an incision. To facilitate cutting, the variable length electrode preferably extends generally transverse to the direction of elongation of the probe at least when the electrode is at least partially extended. Although the variable length electrode concept can be implemented in different ways, first and second electrode supports can be advantageously used for varying the length of the variable electrode. This may be accomplished by mounting the electrode supports on the probe for movement relative to each other to vary the spacing between the electrode supports. The variable length electrode is drivingly coupled to the electrode supports in such a way that the length of the electrode can be varied by varying the spacing between the electrode supports. The spacing between the electrode supports is appropriately controlled to control the length of the electrode. The electrode is coupled to an electrical power supply, which may be conventional, for supplying electrical energy to the electrode for the electrosurgery.

The electrode is preferably flexible and tensioned between the electrode supports so that it can better perform the cutting function. The electrode can cut or coagulate tissue over essentially its full length.

In a preferred implementation, the first electrode support includes a resilient leaf spring, and the leaf spring is coupled to the probe so that it has a free end which is resiliently movable relative to the second electrode support. The electrode is coupled to the leaf spring adjacent the free end so that the leaf spring can tension the electrode and resiliently urge itself away from the other electrode support.

The electrosurgical device preferably includes an elongated, flexible member, and the electrode includes a conductive distal end portion of the flexible member. Accordingly, by relatively moving the flexible member and the probe, the length of the electrode can be controlled.

More specifically, the probe preferably has a generally longitudinally extending passage opening at a port adjacent the distal end of the probe. The flexible member extends through the passage and the port. The second electrode support can advantageously be carried by the probe adjacent the port. With this construction, the flexible member extends over the second electrode support to the leaf spring and is movable relative to the second electrode support.

Preferably, the electrosurgical device includes resilient means for biasing the conductor proximally. This keeps the electrode taut in case the free end of the leaf spring is partially collapsed toward the probe due to inadvertent contact with surrounding knee structure.

Electrical power can be provided to the electrode in various different ways. For example, the second electrode support and at least a region of the distal end portion of the probe may be conductive so that electrical energy can be transmitted through the probe and the second electrode support to the electrode. Alternatively or in addition thereto, the leaf spring may be conductive and electrically coupled to the conductive region of the probe so that the probe and leaf spring can be used to transmit electrical probe and leaf spring can be used to transmit electrical energy to the electrode. As a further alternative, the electrical energy can be supplied through the elongated flexible member to the electrode.

One important feature of this invention is that the danger of inadvertently cutting or charring is materially reduced. For example, the electrode can be fully retracted into the probe for insertion of the probe into the incision. The exposed surfaces of the leaf spring and probe are essentially nonconductive so that the leaf spring and probe cannot cut or burn tissue. When extended in the incision, the electrode ends are set in from the periphery or edges of the leaf spring and probe so that it is difficult to unintentionally contact tissue with the electrode. Finally, if the electrode breaks, the resilient means for biasing the conductor proximally retracts the portion of the electrode proximally of the break into the probe. If desired, the leaf spring can be nonconductive or receive no electrical current so the portion of the electrode distally of the break, which remains with the leaf spring, cannot cause a charring problem.

To assure that substantially all of the current supplied to the electrode is used for cutting or coagulation, the passage through the probe can be used to supply a liquid, such as water, through the port from which the electrode emerges to wash away debris. If this were not done, there may be a current loss. Consequently, less power is required for the surgery, and the likelihood of charring is correspondingly reduced. To assure that only the electrode can cut tissue, the probe and the leaf spring are electrically insulated.

The invention, together with additional features and advantages thereof, may best be understood by reference to the following description taken in connection with the accompanying illustrative drawings.

BRIEF DESCRIPTION OF THE DRAWINGS

FIG. 3 is a fragmentary, axial, sectional view through the distal end portion of the probe assembly.

FIG. 4 is an isometric view with portions of the leaf spring broken away of a portion of the probe assembly.

DESCRIPTION OF THE PREFERRED EMBODIMENT

Figure 1:
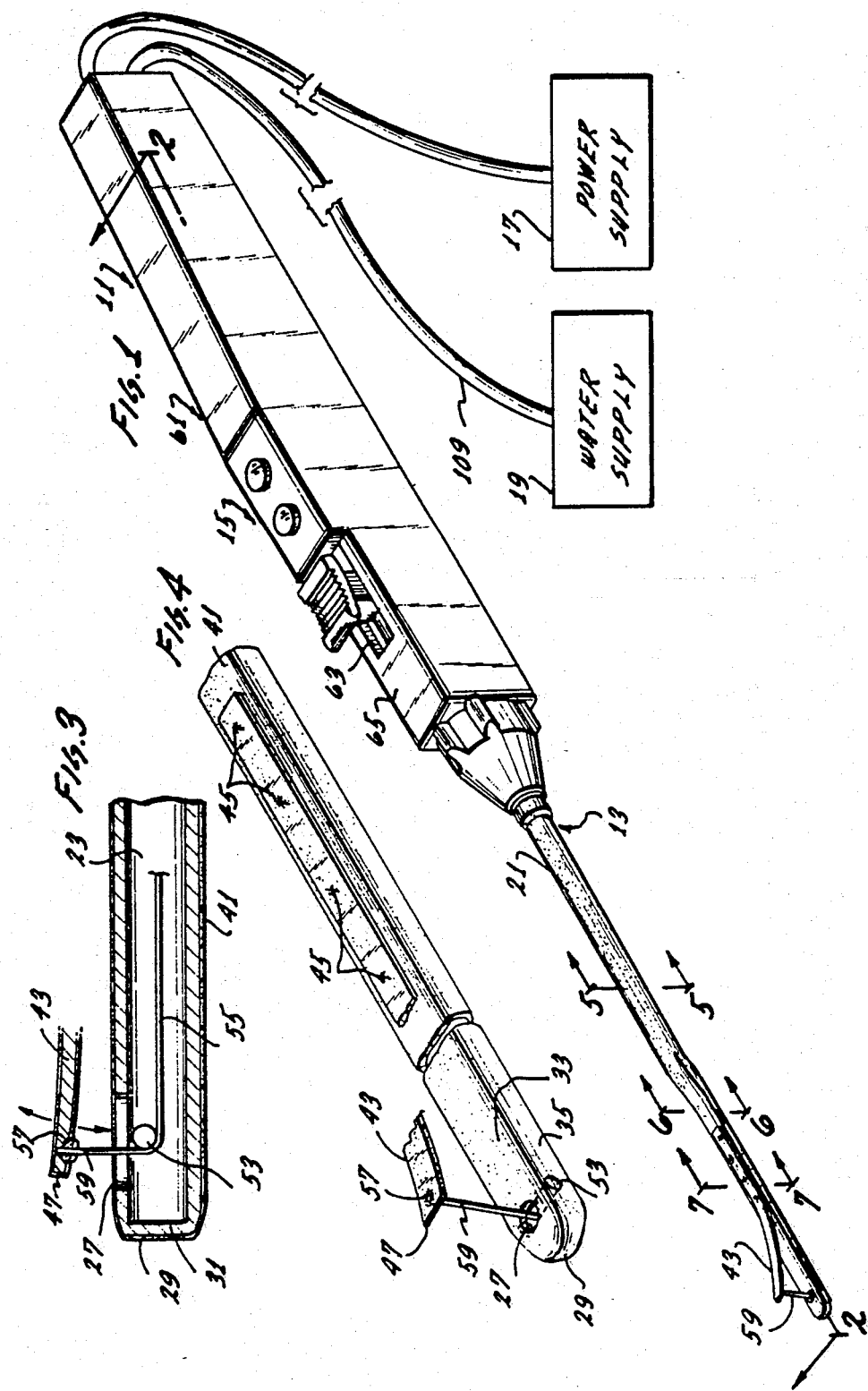
FIG. 1 is an isometric view of an electrosurgical cutting device constructed in accordance with the teachings of this invention.
Figure 2:
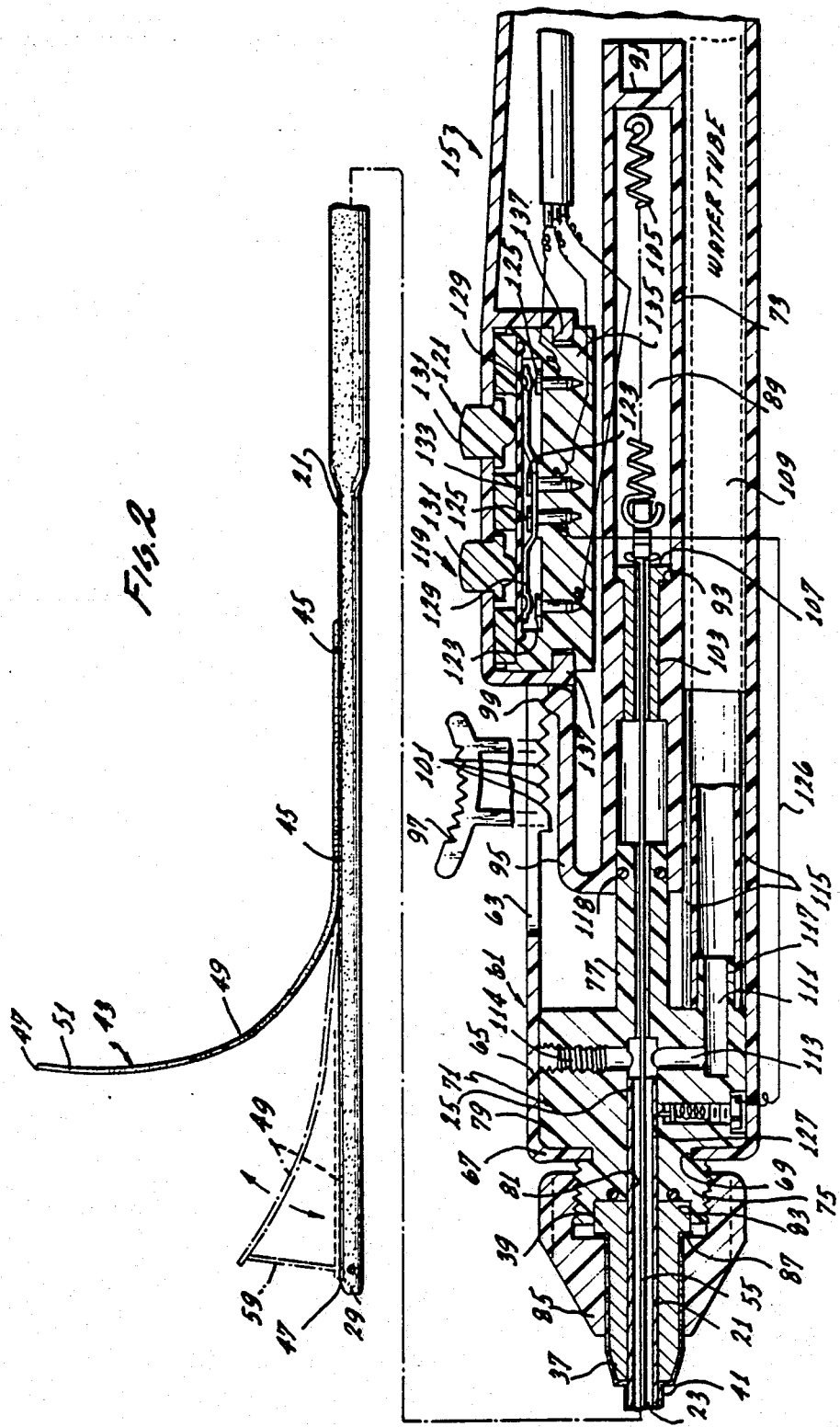
FIG. 2 is a view taken generally along line 2—2 of FIG. 1 with the leaf spring being shown in solid lines in the unrestrained position and in phantom lines in an intermediate position.

FIGS. 1 and 2 show an electrosurgical cutting and coagulating device 11 which generally comprises a probe assembly 13 and a handpiece 15 coupled to an electrical power supply 17 and a water supply 19. Generally, the distal end portion of the probe assembly 13 is insertable through an incision to perform electrosurgery, and the handpiece 15 includes the components necessary to provide control of the surgery. The power supply 17 may be of a type commonly used for electrosurgery, such as Model No. MF-180A which is obtainable from Aspen Laboratories of Englewood, Col.

The probe assembly 13 includes an elongated probe 21, which in this embodiment is of a conductive metal.

Figure 5:
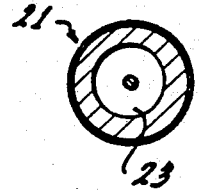
FIGS. 5-7 are enlarged sectional views taken generally along line 5—5, line 6—6 and line 7—7, respectively, of FIG. 1.
Figure 6:
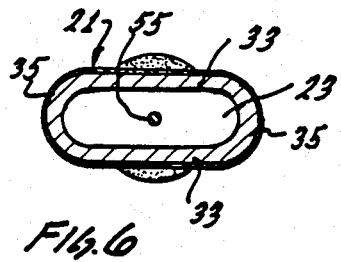
Figure 7:
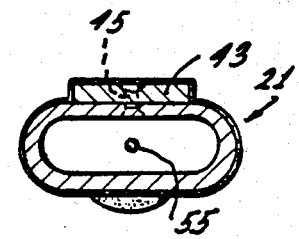

The probe 21 has an elongated, axial passage 23 extending from a proximal end 25 (FIG. 2) of the probe and opening at a port 27 (FIGS. 3) closely adjacent a distal end 29. The passage 23 is closed at the distal end 29 by an end wall 31 (FIG. 3). Proximal regions of the probe 21 are of generally circular cross section as shown in FIG. 5, and more distal regions of the probe are somewhat flattened as best shown in FIGS. 6 and 7 to facilitate entry into an incision during use of the device 11. At the region shown in FIG. 6, the probe has spaced generally flat walls 33 joined by generally semi-cylindrical end walls 35.

The probe assembly 13 also includes a bushing 37 (FIG. 2) having an axial passage therethrough for receiving the probe 21. The probe 21 extends completely through the bushing 37 and is suitably attached thereto as by a suitable epoxy. The bushing 37 has an annular flange 39 at its proximal end for use in attachment of the probe assembly 13 to the handpiece 15. The probe 21 and the bushing 37 are constructed of a suitable, electrically conductive metal, and the entire exposed outer surface of the probe distally of the bushing 37, as well as the entire outer surface of the bushing 37 distally of the flange 39, is covered with an electrical insulating jacket 41. The insulating jacket 41 may be a suitable, non-conductive plastic material, which is applied as by spraying on certain surfaces of the probe assembly 13.

An electrode support in the form of a resilient, flexible leaf spring 43 of a conductive metal is attached to one of the flat walls 33 of the probe 21 in any suitable manner, such as by spot welds 45 (FIG. 4). As shown in FIG. 7, the leaf spring 43 is in direct metal-to-metal contact with the probe 21 so that there is electrical contact between them. The insulation jacket 41 is applied to the probe 21 and the leaf spring 43 after the leaf spring is spot welded to the probe. The insulation jacket 41 also covers all of the exposed outer surfaces of the leaf spring 43. A length of the leaf spring 43 projects upwardly (as viewed in FIG. 2) from the probe 21 to a free end 47. The leaf spring 43 can be deflected downwardly (as viewed in FIG. 2) through a plurality of intermediate positions to a fully retracted position in which it lies along the flat wall 33 with its free end 47 lying just proximally of the distal end 29 of the probe 21.

In the unrestrained condition, the leaf spring 43 is generally in the shape of the condyle, and this facilitates its use within the confined area of the knee. In the illustrated embodiment, the leaf spring 43 in the unrestrained condition has an arcuate section 49 and a generally linear section 51 adjacent the free end 47. Although the leaf spring 43 can be designed to have the desired spring rate, in the embodiment illustrated, the spring rate is variable, and the leaf spring provides substantially greater force in the flattened or retracted position than in the unrestrained position.

An electrode support or bearing which, in this embodiment, is in the form of a conductive pin 53 (FIGS. 3 and 4) is mounted on the probe 21 within the passage 23 in registry with the port 27. For example, the opposite ends of the pin may be received within correspondingly shaped openings in the probe 21 and coined to retain the ends of the pin in position on the probe.

The probe assembly 13 also includes an uninsulated, conductive, elongated flexible member, which may be a braided wire 55 of a suitable metal, such as a tungsten-rhenium alloy. The braid may comprise 0.001 inch fibers. A flexible member of this type may be of small diameter, such as about 0.005 to 0.007 inch and, as such, it provides a high current density when in use. When constructed in this manner, the flexible member is relatively limp.

The flexible member 55 is attached at one end to the leaf spring 43 closely adjacent the free end 47, and it extends through the port 27 and part-way around the pin 53. The flexibility of the flexible member is sufficient so that it can readily slide over the pin 53 and make about a 90-degree turn. From the pin 53, the flexible member 55 extends axially through the passage 23 to a location within the handpiece 15 as shown in FIG. 2 and described more fully hereinbelow. In this regard, the pin 53 is positioned so that it will guide the flexible member 55 coaxially in the passage 23.

The distal end of the flexible member 55 may be attached to the leaf spring 43 in any suitable manner, such as by solder 57 (FIG. 3) which retains the flexible member within an opening in the leaf spring. With this construction, the exposed length of the flexible member, which is essentially the length of the flexible member 55 between the pin 53 and the leaf spring 43, defines an electrode 59 which can be used for electrosurgery.

By pulling the flexible member 55 proximally, the leaf spring 43 is moved toward the flattened position to reduce the length of the electrode 59. Conversely, by releasing the flexible member 55, the leaf spring 43 pulls the flexible member in the other direction to lengthen the electrode 59. Accordingly, the electrode 59 is a variable-length electrode, and it is drivingly coupled to the pin 53 and the leaf spring 43, both of which form electrode supports, so that the length of the electrode can be varied by varying the spacing between the leaf spring and the pin. Thus, the leaf spring 43 urges itself away from the pin 53, and adjusting means, which includes the flexible member 55 and means within the handpiece 15, control the extent to which the leaf spring can lengthen the electrode.

The flexible member 55 and the electrode 59 are preferably sufficiently flexible so that the electrode must be tensioned to hold it taut. The electrode 59 is tensioned by the leaf spring 43 and by whatever is used to retain the proximal end of the flexible member 55 in position. The electrode 59 extends generally transverse to the direction of elongation of the probe 21, and the length of the electrode is reduced to substantially zero when the flexible member 55 is pulled to flatten the leaf spring 43 against the probe 21.

The port 27 is in the wall 33 and, thus, forms a radial opening in the passage 23. The port 27 is spaced proximally of the distal end 29 of the probe and inwardly of the walls 35 so that the proximal end of the electrode 59 is surrounded by insulated portions of the probe 21 to reduce the likelihood of inadvertent burning or charring. For the same reason, the distal end of the electrode 59 is preferably attached to the leaf spring 43 by the solder 57 at a location spaced proximally of the free end 47 and inwardly of the periphery of the leaf spring.

The handpiece 15 is used to mount the probe assembly 13 and to control the tensioning of the flexible member 55 and the supply of water and electrical energy to the electrode 59. The handpiece 15 includes a housing 61 (FIGS. 1 and 2) which includes two or more housing sections suitably interconnected as by sonic welding so as to permit assembly of the handpiece. The housing 61, which is preferably constructed of a nonconductive plastic material, has a longitudinally extending slot 63 in an upper wall 65 of the housing and a forward wall 67 with an opening 69 (FIG. 2).

The handpiece 15 also includes a mounting block 71 suitably mounted within the forward regions of the housing 61, such as by fasteners (not shown) or an adhesive and a slidable controller 73. The mounting block 71, which is constructed of suitable, nonconductive plastic, has a threaded boss 75 at its distal end and an axially extending shaft 77 at its proximal end. The boss 75 and the shaft 77 are both of lesser cross-sectional area than a central main body portion 79 of the mounting block 71. A passage 81 extends axially completely through the mounting block 71.

The boss 75 projects through the opening 69 and out of the housing 61. The probe 21 is received within the passage 81, and the flange 39 of the bushing 37 is received within a counterbore 83 of the mounting block 71. The handpiece 15 also includes a nut 85 threaded onto the boss 75 and having an annular shoulder 87 for engaging the flange 39 to mount the probe 21 on the handpiece 15.

Although the controller 73 can be of various different constructions, in the embodiment illustrated, it is in the form of an elongated tube of a suitable plastic material having an axial passage 89 which is open at its distal end to slidably receive the shaft 77 and is closed at its proximal end by an end wall 91. A central region of the passage 89 is of reduced diameter and defines a shoulder 93 at one end.

The controller 73 also has a resilient arm 95 with an upstanding button 97 which projects through the slot 63 and out of the housing 61. The resilient arm 95 terminates in a lug 99 which cooperates with a series of teeth 101 formed on the inside surface of the wall 65 of the housing 61 along one side of the slot 63. By pushing inwardly on the button 97, the arm 95 deflects inwardly to separate the lug 99 from the teeth 101 so that the controller 73 can be slid longitudinally along the shaft 77 to a new position. At the new position, the inward force on the button 97 is released to allow the resilient arm 95 to move upwardly to place the lug 99 into engagement with the adjacent pair of teeth 101 to thereby lock the controller 73 in the new longitudinal position.

The handpiece 15 also includes a coupling 103 slidably received in a central region of the passage 89 and a coil compression spring 105 having one end affixed to the controller 73 adjacent the end wall 91 and its other end attached to the coupling 103. The proximal end of the flexible member 55 extends through the passage 81 of the mounting block 71, partially through the passage 89 of the controller 73 and through the passage of the coupling 103 and is affixed to the coupling 103. The coupling 103 has a circumferential flange 107 which normally engages the shoulder 93.

When assembled in this fashion, the leaf spring 43 tends to pull the flexible member 55 proximally, and the spring 105 biases the flexible member in the opposite direction. The force of the leaf spring 43 is greater than the force of the spring 105 so that, absent external forces acting on the leaf spring 43, the flange 107 is held in engagement with the shoulder 93 as shown in FIG. 2.

Water can be supplied to the passage 23 of the probe 21 by conduit means which includes a tube 109 coupled to the water supply 19, an axial bore 111 in the mounting block 71 and a radial bore 113 in the mounting block which communicates with the passage 81. The radial bore 113 may extend from the axial bore 111 in the mounting block 71 and be plugged at the other end by a plug 114. One end of the tube 109 is retained between ribs 115 on the housing 61 and that end of the tube 109 is also slipped over a tubular fitting 117 on the mounting block 71. The water supplied by the tube 109 also flows proximally through the passage 81 into the passage 89 of the controller 73. A seal 118 prevents leakage of the water from the passage 89 into the surrounding regions of the housing 61.

The handpiece 15 also includes a cut switch 119 and a coagulate switch 121. The cut switch 119 comprises contacts 123 and 125 coupled, respectively, to the power supply 17 (FIG. 1) and to the probe 21 through a conductor 126 and a spring-biased contact 127 (FIG. 2). The switch 119 also includes a resilient blade 129 and a button 131. The switch 121 is identical to the switch 119, and corresponding parts are designated by corresponding reference numerals. A diaphragm 133 extends between the buttons 131 and the associated blades 129 to provide a seal. The contacts 123 and 125 and the blades 129 can be carried by a switch block 135 suitably mounted within the housing 61 as by flanges 137. The contacts 123 and 125 of the coagulate switch 121 are electrically coupled to the contact 125 of the cut switch 119 and the power supply, respectively.

Figure 9:
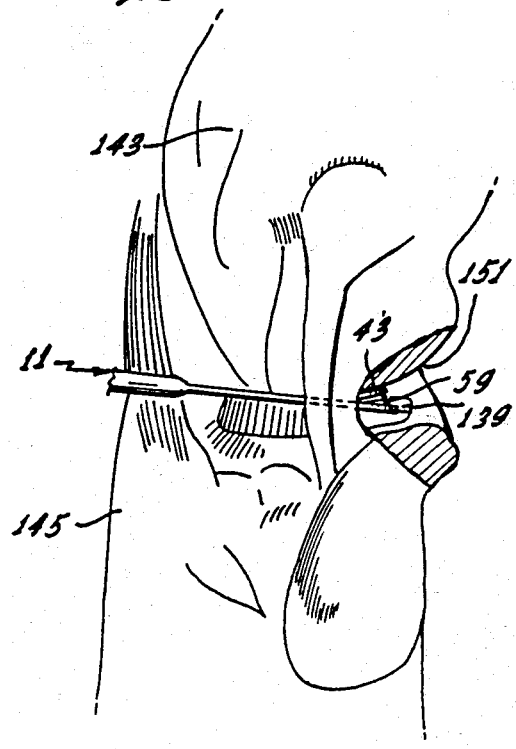
FIG. 9 is a sectional view taken generally along line 9—9 of FIG. 8.
Figure 8:
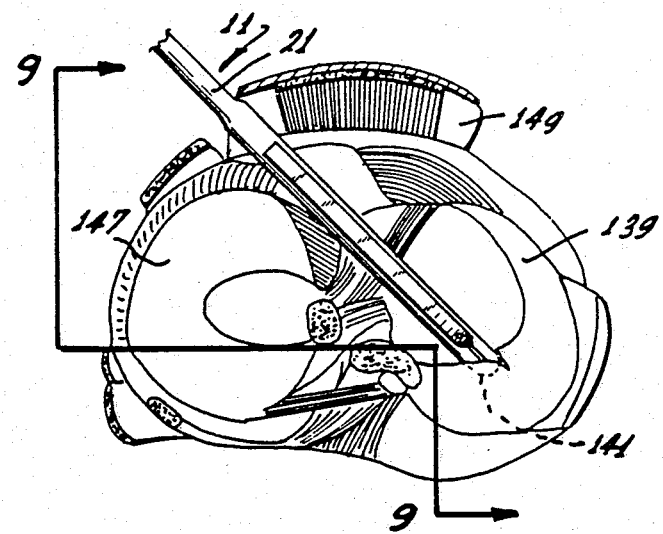
FIG. 8 is a sectional view looking downwardly on the left knee just above the menisci and illustrating the use of the electrosurgical device.

FIGS. 8 and 9 show how the electrosurgical device 11 can be used to remove the region of the medial meniscus 139 which contains a tear 141. As shown in FIGS. 8 and 9, the knee joint is formed between the femur 143 and the tibia 145 and includes the medial meniscus 139, a lateral meniscus 147 and a patella 149.

To perform the surgery, an incision is made in the lateral anterior region of the knee, and the distal end portion of the probe 21 is inserted into the incision, with the electrode 59 in the fully retracted position. Of course, the incision may be made elsewhere, such as in the anterior medial or anterior lateral regions of the knee. The electrode 59 may be moved to the fully retracted position in which the leaf spring 43 lies along the flat wall 33 as shown in dashed lines in FIG. 2 by depressing the button 97 and moving the controller 73 proximally to the most proximal position as shown in FIG. 2. This minimizes the cross-sectional dimensions of the portions of the probe assembly 13 which are to be inserted into the incision and gives the electrode an essentially zero length. For example, the height dimension of the probe 21 and the collapsed leaf spring 43, i.e., the vertical dimension as viewed in FIG. 7, may be about 3 millimeters. The width or horizontal dimension of the probe 21 is much less important.

With the probe 21 properly positioned within the knee, the surgeon depresses the button 97 and moves the controller 73 distally so that the leaf spring 43 pulls on the flexible member 55 to lengthen the electrode 59 the desired amount, whereupon the button 97 is released to allow the lug 99 to engage an adjacent pair of the teeth 101 to retain the controller 73 in this position. The leaf spring 43 in this position is generally configured to lie along the condyle 151. For example, the maximum length of the electrode 59 may be about 10 millimeters.

Undamped sinusoidal electrical energy is then applied to the electrode 59 by closing the cut switch 119. Closure of the cut switch 119 is sensed by the power supply 17 which then supplies appropriate electrical energy to contacts 123 and 125 of the switch 119 to obtain the desired cutting action at the electrode 59. Closure of the cut switch 119 provides a conductive path to the electrode 59 via the conductor 126, the contact 127, probe 21 and the electrode support 53. If the coagulate switch 121 is closed, the power supply senses such closure and supplies appropriate electrical energy to the contacts 123 and 125 of the coagulate switch to obtain the desired coagulating action at the electrode 59. If the coagulate switch 121 is closed, damped sinusoidal current is supplied to the conductor 126 via the contact 125, the switch blade 129, and contact 123 of the switch 121, and the contact 125 of the switch 119. The circuit is completed from the electrode 59 through the patient and a ground pad (not shown) in a conventional manner. Electrical contact between the electrode 59 and the electrode support 53 is maintained as the flexible member 55 slides over the electrode support 53.

Water, or other nonionic solution, is supplied by opening a valve (not shown) to supply water from the water supply 19 through the tube 109, the passage 23 and the port 27 to the region adjacent the electrode 59 to wash away debris that may form during the cutting operation. The water from the port 27 and the electrode 59 is essentially coaxial. The water and debris are suctioned off using appropriate equipment (not shown) and conventional techniques. The electrode 59 cuts the meniscus in any desired direction to remove the region of the meniscus 139 containing the tear 141. The cutting action proceeds safely and rapidly, and the line along which the cut is formed is smooth.

Although an exemplary embodiment of the invention has been shown and described, many changes, modifications and substitutions may be made by one having ordinary skill in the art without necessarily departing from the spirit and scope of this invention.

I claim:
1. An electrosurgical device comprising:
an elongated probe having a distal end portion for insertion into an incision;
first and second electrode supports;
means for mounting the electrode supports on the probe, said first and second electrode supports being movable relative to each other to vary the spacing between the first nd second electrode supports;
a variable length flexible electrode for electrosurgery extending between the first and second electrode supports so that the length of the electrode can be varied by varying the spacing between the first and second electrode supports;
means for controlling the spacing between the first and second electrode supports to thereby control the length of the electrode;
means couplable to an electrical power supply for supplying electrical energy to the electrode for electrosurgery; and
the first electrode support includes a resilient leaf spring, said mounting means couples the leaf spring to said probe so that the leaf spring has a free end which is resiliently movable relative to said second electrode support, and said electrode is coupled to said leaf spring adjacent said free end whereby the leaf spring can tension the electrode.

2. An electrosurgical device as defined in claim 1 wherein the probe is elongated and the variable length electrode extends generally transverse to the direction of elongation at least when the electrode is at least partially extended.

3. An electrosurgical device as defined in claim 1 wherein the variable length electrode has a minimum length of substantially zero to facilitate insertion of the distal end of the probe into the incision.

4. An electrosurgical device as defined in claim 1 wherein said controlling means includes an elongated flexible member, said electrode includes a distal end portion of the flexible member, and said controlling means includes means for moving the flexible member relative to said probe to control the position of the leaf spring.

5. An electrosurgical device as defined in claim 4 wherein said probe has a generally longitudinally extending passage opening at a port adjacent the distal end of the probe, said flexible member extends along said passage and exits said passage through said port, and said second electrode support is carried by the probe adjacent the port.

6. An electrosurgical device as defined in claim 5 including conduit means for supplying a liquid to said passage for washing away debris which would impair the electrosurgery.

7. An electrosurgical device as defined in claim 4 wherein said flexible member has a proximal end and said electrosurgical device includes resilient means for biasing the flexible member proximally against the biasing force of the leaf spring.

8. An electrosurgical device as defined in claim 5 wherein said electrical energy-supplying means includes said second electrode support and at least a region of the probe being conductive and said second electrode and said region of the probe are electrically coupled.

9. An electrosurgical device as defined in claim 1 including an electrical insulating coating on said distal end portion of said probe and said leaf spring.

10. An electrosurgical device comprising:
an elongated probe having a distal end portion and a generally longitudinally extending passage opening at a port adjacent the distal end of the probe, said probe being adapted for insertion into an incision;
an elongated flexible member having proximal and distal end portions, said flexible member extending along said passage and being extendible through said port, and said proximal end portion of said flexible member being releasably fixable against movement in said passage;
a leaf spring carried by said probe and having a free end, said leaf spring being coupled to the distal end portion of said flexible member and the resilience of the leaf spring tending to pull a length of the flexible member out through said port; and
a length of the flexible member outside of the port forming an electrode for electrosurgery and the length of the electrode being variable by moving the flexible member relative to the probe.

11. An electrosurgical device as defined in claim 10 wherein the electrode includes braided fibers.

12. An electrosurgical device as defined in claim 10 including an electrode support carried by said probe in said passage adjacent said port and said elongated flexible member extends from said electrode support to said port, and said elongated flexible element being movable relative to the electrode support.

13. An electrosurgical device as defined in claim 12 wherein at least a region of said probe is conductive and said electrode support is conductive and coupled to said region of said probe, at least a distal end portion of said flexible member is conductive, and said distal end portion of said flexible member is engageable with said electrode support.

14. An electrosurgical device as defined in claim 10 wherein said leaf spring has a periphery, said flexible member is coupled to the leaf spring inwardly of the periphery and adjacent said free end and at least the exposed regions of the leaf spring are essentially nonconductive.

15. An electrosurgical device as defined in claim 10 wherein said port opens radially and is spaced proximally of said distal end of the probe.

16. An electrosurgical device as defined in claim 10 wherein said electrode extends out of said port in a direction which is generally transverse to the direction of elongation of the probe at all lengths of the variable length electrode.

17. An electrosurgical device comprising:
a probe assembly including an elongated probe having a distal end portion for insertion into an incision, an elongated flexible member, means including a distal end portion of the flexible member for forming a variable length electrode which is carried by the distal end portion of the probe, and said flexible member being movable relative to the probe to vary the length of the electrode;
a handpiece which can be manually grasped;
means for attaching the probe assembly to the handpiece;
said handpiece including means for moving the flexible member to vary the length of the electrode;
means couplable to an electrical power supply for supplying electrical energy to the electrode for electrosurgery;
means for tensioning the electrode; and
said tensioning means including the handpiece comprising first resilient means for biasing the flexible member in one direction and the probe assembly including second resilient means for biasing the flexible member in the other direction with the force exerted on the flexible member by the second resilient means being greater than the force exerted on the flexible member by the first resilient means, said first resilient means retracting at least a portion of the electrode if the electrode breaks.

18. An electrosurgical device as defined in claim 17 wherein said moving means includes a movable controller and means for fixing the controller in any of a plurality of positions and said surgical device includes means for coupling the flexible member and the controller.

19. An electrosurgical device a defined in claim 17 wherein said electrical energy supplying means includes aid probe having a conductive region and said handpiece includes conductive means engageable with the conductive region of the probe.

* * * * *